United States Patent
Chowaniec et al.

(10) Patent No.: US 10,111,658 B2
(45) Date of Patent: Oct. 30, 2018

(54) DISPLAY SCREENS FOR MEDICAL DEVICES

(71) Applicant: Covidien LP, Mansfield, MA (US)

(72) Inventors: Matthew Chowaniec, Middletown, CT (US); Michael Ingmanson, Stratford, CT (US); Xingrui Chen, Hamden, CT (US); Steven Plachtyna, North Haven, CT (US)

(73) Assignee: Covidien LP, Mansfield, MA (US)

( * ) Notice: Subject to any disclaimer, the term of this patent is extended or adjusted under 35 U.S.C. 154(b) by 117 days.

(21) Appl. No.: 14/620,888

(22) Filed: Feb. 12, 2015

(65) Prior Publication Data
US 2016/0235402 A1 Aug. 18, 2016

(51) Int. Cl.
*A61B 17/068* (2006.01)
*A61B 17/072* (2006.01)
(Continued)

(52) U.S. Cl.
CPC .......... *A61B 17/068* (2013.01); *A61B 17/072* (2013.01); *A61B 34/30* (2016.02); *A61B 90/361* (2016.02); *G06F 1/1637* (2013.01); *G06F 1/1643* (2013.01); *G06F 1/1656* (2013.01); *G06F 1/1694* (2013.01); *G06F 3/0346* (2013.01); *G06F 3/0485* (2013.01); *G06F 3/04883* (2013.01); *G06F 19/3481* (2013.01); *G16H 40/63* (2018.01); *A61B 2017/00022* (2013.01); *A61B 2017/0046* (2013.01); *A61B 2017/00115* (2013.01); *A61B 2017/00199* (2013.01); *A61B 2017/00225* (2013.01);
(Continued)

(58) Field of Classification Search
CPC .......... A61B 17/068; A61B 2090/368; G06F 2200/1614; G06F 3/0346
See application file for complete search history.

(56) References Cited

U.S. PATENT DOCUMENTS

| 6,716,233 B1 | 4/2004 | Whitman |
| 7,077,856 B2 | 7/2006 | Whitman |

(Continued)

FOREIGN PATENT DOCUMENTS

| EP | 2756808 A1 | 7/2014 |
| WO | 2012109760 A1 | 8/2012 |
| WO | 2013018908 A1 | 2/2013 |

OTHER PUBLICATIONS

European Search Report completed on Jun. 29, 2016 in corresponding European Patent Application No. 16155271, 2 pages.

*Primary Examiner* — Michael Faragalla
*Assistant Examiner* — Chayce Bibbee

(57) ABSTRACT

An electromechanical handheld surgical device includes a housing, and a non-planar display screen. The housing encloses a processor, a memory storing instructions, and an orientation detector configured to detect orientation of the electromechanical handheld surgical device with respect to a reference direction. The non-planar display screen is fixedly attached around a portion of the housing and configured to display information. Then instructions, when executed by the processor, cause the non-planar display screen to display the information on a portion of the non-planar display screen. The portion of the non-planar display screen is determined by the processor based on the detected orientation.

23 Claims, 10 Drawing Sheets

(51) Int. Cl.
 *G06F 1/16* (2006.01)
 *A61B 34/30* (2016.01)
 *G06F 3/0485* (2013.01)
 *G06F 3/0488* (2013.01)
 *G06F 3/0346* (2013.01)
 *G06F 19/00* (2018.01)
 *G16H 40/63* (2018.01)
 *A61B 17/00* (2006.01)
 *A61B 90/00* (2016.01)
 *A61B 34/20* (2016.01)

(52) U.S. Cl.
 CPC ............... *A61B 2034/2048* (2016.02); *A61B 2034/2059* (2016.02); *A61B 2090/067* (2016.02); *A61B 2090/365* (2016.02); *A61B 2090/368* (2016.02)

(56) References Cited

U.S. PATENT DOCUMENTS

| | | |
|---|---|---|
| 8,696,650 B2 | 4/2014 | Quick et al. |
| 2005/0020909 A1 | 1/2005 | Moctezuma de la Barrera et al. |
| 2011/0121049 A1 | 5/2011 | Malinouskas et al. |
| 2011/0125138 A1 | 5/2011 | Malinouskas et al. |
| 2012/0050331 A1 | 3/2012 | Kanda |
| 2012/0116364 A1* | 5/2012 | Houser ............ A61B 17/00234 606/1 |
| 2014/0175148 A1 | 6/2014 | Whitman |
| 2015/0272572 A1* | 10/2015 | Overmyer .............. A61B 90/98 227/177.1 |
| 2015/0355677 A1* | 12/2015 | Breedvelt-Schouten .................... G02B 27/0093 345/419 |

\* cited by examiner

DISPLAY SCREENS FOR MEDICAL DEVICES

BACKGROUND

1. Technical Field

The present disclosure relates to a flexible or curved display screen. More specifically, the present disclosure relates to a non-planar, flexible or curved display screen to display information about surgical devices and surgical operations thereon.

2. Background of Related Art

Traditionally, electromechanical handheld surgical devices have had a static label describing usages thereof, which is affixed to a surface thereof. However, such a static label cannot describe all features due to limited space of the static label. Even if the static label is sufficiently large to describe all features of the electromechanical handheld surgical device, additional information is necessary when the electromechanical handheld surgical device is used by a clinician who uses a language different from the language printed on the static label. Thus, it is practically impossible to provide information in multiple languages on such a static label.

Further, in a case when the electromechanical handheld surgical device is capable of receiving several types of end effectors for different surgical operations, the static label is impractical to provide sufficient information for different end effectors due to the limited space of the static label.

Recently, electromechanical handheld surgical devices have been developed and include software which performs functional modules of the electromechanical handheld surgical device. Such software is typically updated periodically, wherein a display screen of the electromechanical handheld surgical device must be dynamic and updated or changed to correspond to the updated software. Thus, static labels cannot dynamically show relevant information in accordance with updates to the software or to the modes of operation of the electromechanical handheld surgical device.

Further, surgical devices have been used in diverse surgical operations, which include biopsy, sealing, cutting, cauterizing, coagulating, desiccating, etc. While performing these surgical operations, clinicians need dynamic information about surgical operations and surgical sites of patients under the surgical operations. Some surgical devices have a flat display screen to show this dynamic information. However, the size of the flat display screen is restricted based on the size and the structure of the housing of the electromechanical handheld surgical device. Further, rigidity of the flat display screen also restricts the maximum size of the flat display screen that can be installed on the electromechanical handheld surgical device, the surface of which is typically not flat.

Surgical devices are generally designed for ease of use for clinicians. Ergonomic designs are employed into structure of the electromechanical handheld surgical devices. One of the ergonomic design elements employed in electromechanical handheld surgical devices is the provision of a curved outer housing. However, due to this curved outer housing, the incorporation of a flat display screen is also restricted in size and may result in waist of space inside of the curved outer housing in order to accommodate the flat display screen.

Thus, it is desirable that surgical devices have a flexible or curved display screen that better fits the ergonomic design of surgical devices, saves space inside of the housing of the electromechanical handheld surgical devices, and displays dynamic information thereon. Accordingly, a need exists for handheld surgical devices to have a flexible or curved display screen.

SUMMARY

The present disclosure relates to non-planar display screen for an electrosurgical handheld surgical device. The non-planar display screen may have a larger surface area than a flat or planar display screen and may display dynamical information about the surgical device and/or the surgical procedure. Further, the non-planar display screen may save space for the electromechanical handheld surgical device so that the size of the electromechanical handheld surgical device may be minimized. Furthermore, the non-planar display screen may fit to the ergonomic design of the electromechanical handheld surgical device.

According to an aspect of the present disclosure, the electromechanical handheld surgical device includes a housing, and a non-planar display screen. The housing encloses a processor, a memory storing instructions, and an orientation detector configured to detect orientation of the electromechanical handheld surgical device with respect to a reference direction. The non-planar display screen is fixedly attached around a portion of the housing and configured to display information. Then instructions, when executed by the processor, cause the non-planar display screen to display the information on a portion of the non-planar display screen. The portion of the non-planar display screen is determined by the processor based on the detected orientation.

The portion of the non-planar display screen may be determined with respect to the reference direction.

The reference direction may be in line with a direction of gravity.

A starting location of the portion of the non-planar display screen may be located on the non-planar display screen at a constant angle with respect to the reference direction.

A middle of the portion of the non-planar display screen may be located on the non-planar display screen at a constant angle with respect to the reference direction.

An ending location of the portion of the non-planar display screen may be located on the non-planar display screen at a constant angle with respect to the reference direction.

The information may be related to a surgical operation when the electromechanical handheld surgical device is used in the surgical operation.

The information may change based on a status of the surgical operation.

The information may be related to the electromechanical handheld surgical device before the electromechanical handheld surgical device is used in a surgical operation.

The information may be related to a portion of tissue to which a surgical operation is performed.

The non-planar display screen may be touch-sensitive. The displayed information may be scrolled based on a direction of a touch to the non-planar display screen.

The non-planar display screen may be curved or flexible. The non-planar display screen may extend greater than about 15° around a portion of the housing.

According to a further aspect of the present disclosure, a method for displaying information on a non-planar display screen fixedly attached around a portion of an electromechanical handheld surgical device is provided. The method includes obtaining an orientation with respect to a reference orientation from an orientation detector of the electromechanical handheld surgical device, determining a portion of the non-planar display screen based on the orientation and with respect to the reference orientation, retrieving status information from the electromechanical handheld surgical device, and displaying information on the portion of the non-planar display screen based on the status information of the electromechanical handheld surgical device.

In an embodiment, displaying information includes displaying information about the electromechanical handheld surgical device when the status information indicates that the electromechanical handheld surgical device is not used in a surgical operation.

In another embodiment, displaying information includes displaying information about a surgical operation when the status information indicates that the electromechanical handheld surgical device is being used in the surgical operation.

In still another embodiment, displaying information includes displaying information related to a portion of tissue to which a surgical operation is performed, when the status information indicates that the electromechanical handheld surgical device is used in the surgical operation.

The reference orientation may be in line with a direction of gravity.

The method may further include determining whether an end effector is connected to the electromechanical handheld surgical device.

According to a further aspect of the present disclosure, an electromechanical surgical system is provided. The surgical system includes a support immovably fixed to a surface, an electromechanical surgical device configured to perform a surgical operation, a plurality of arms, and a plurality of display screens. One end of the plurality of arms is connected to the electromechanical surgical device and the other end of the plurality of arms is connected to the support. Each one of the plurality of non-planar display screens is fixedly attached around a corresponding one of the plurality of arms. Each arm includes a sensor configured to periodically capture an image of a view under each arm, and an orientation detector configured to detect an orientation of each arm with respect to a reference orientation and the non-planar display screen corresponding to each arm displays a captured image on a portion of the display screen of each arm based on the detected orientation.

BRIEF DESCRIPTION OF THE DRAWINGS

Embodiments of the present disclosure are described herein with reference to the accompanying drawings, wherein.

DETAILED DESCRIPTION OF EMBODIMENTS

Embodiments of the presently disclosed flexible or curved display screen for electromechanical handheld surgical devices are described in detail with reference to the drawings.

Figure 1:
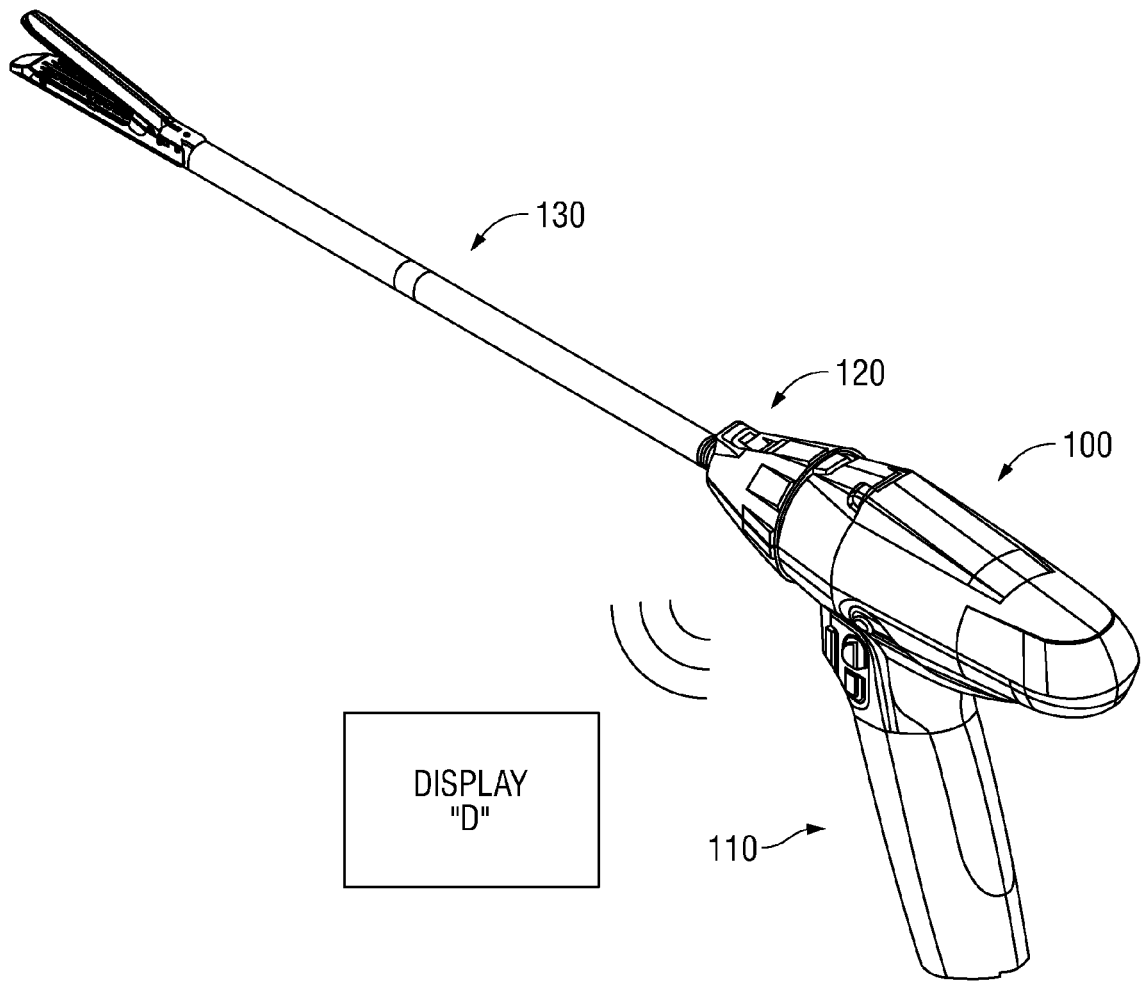
FIG. 1 is a perspective view of an electromechanical handheld surgical device of the prior art.

FIG. 1 illustrates an electromechanical handheld surgical device 100 of the prior art, which includes a handle 110 and a selective connection part 120, which can be connected with end effectors 130 or single use loading units. A clinician can hold and operate handle 110 to perform a surgical operation with electromechanical handheld surgical device 100. When a clinician uses electromechanical handheld surgical device 100, there is a display screen "D" separate from electromechanical handheld surgical device 100, at which the clinician looks to for information pertinent to the surgical operation, which is transmitted from electromechanical handheld surgical device 100 to the display screen "D". In this situation, since the display screen "D" is separate from electromechanical handheld surgical device 100, looking at the display screen "D" away from electromechanical handheld surgical device 100, may take the clinician's vision away from the surgical site.

Figure 2:
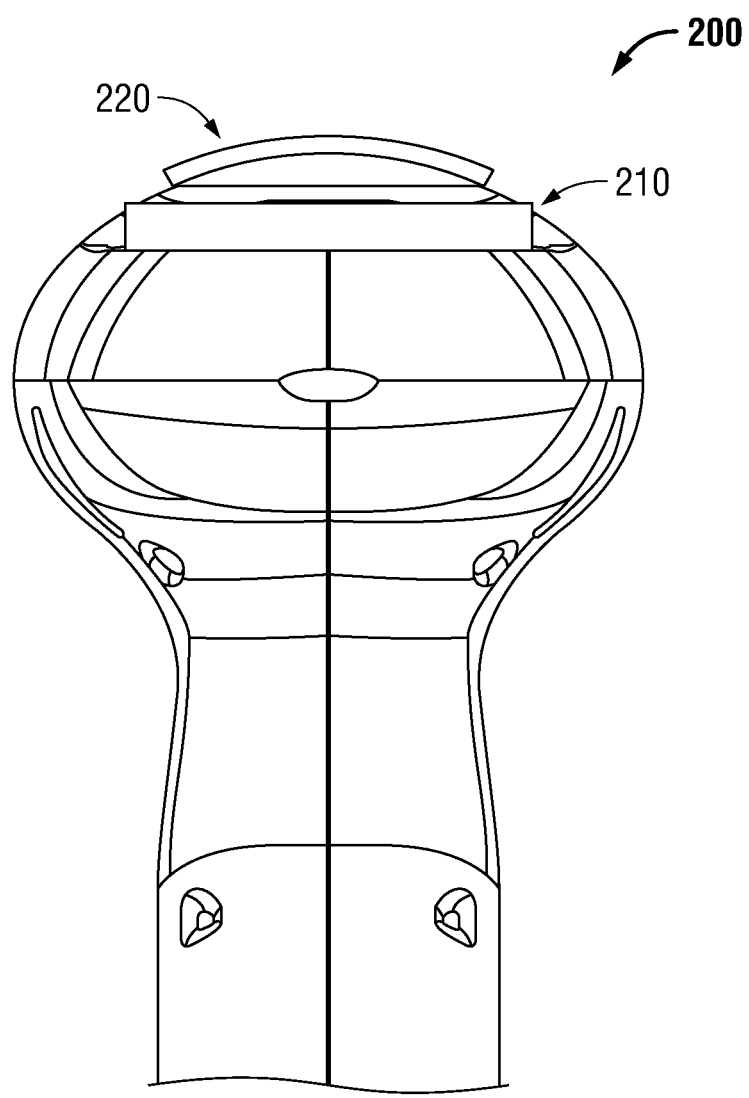
FIG. 2 is a rear view of the electromechanical handheld surgical device of FIG. 1 including a display screen of the prior art.

In another situation, an electromechanical handheld surgical device includes a display screen in or on the electromechanical handheld surgical device. FIG. 2 illustrates such a situation and shows a rear view of an electromechanical handheld surgical device 200 of the prior art, which includes a flat display screen 210. The electromechanical handheld surgical device 200 further includes a protector, shell, or cover 220 to protect flat display screen 210 from possible impacts to flat display screen 210. Information related to electromechanical handheld surgical device 200 or surgical operations may be displayed on flat display screen 210. The flat display screen 210 is generally installed at the top of electromechanical handheld surgical device 200 right under protector 220.

Clinicians are capable of viewing relevant information of electromechanical handheld surgical device 200 or surgical operations on flat display screen 210, while performing surgical operations using electromechanical handheld surgical device 200. Nevertheless, due to location of flat display screen 210, clinicians may have to hold electromechanical handheld surgical device 200 in an upright position or bend or twist their neck to look at the information displayed on display screen 210 due to a non-upright orientation of electromechanical handheld surgical device 200 during the surgical operation.

As shown in FIGS. 1 and 2, electromechanical handheld surgical devices 100 and 200 of the prior art have ergonomic designs, e.g., a curved housing or enclosure, for functional and/or esthetic purposes. However, due to these ergonomic designs, some space between flat display screen 210 and the curved housing of electromechanical handheld surgical device 100 or 200 is wasted. For example, as seen in FIG.

2, there is a space (e.g., wasted space) between flat display screen 210 and protector 220.

Further, when flat display screen 210 is installed inside of the curved housing or enclosure of electromechanical handheld surgical device 200, some spaces are inevitably wasted. Furthermore, display screen 210 is substantially rigid, and this rigidity of flat display screen 210 also limits a maximum size of flat display screen 210 that can fit to the curved housing of electromechanical handheld surgical device 200.

Figure 3A:
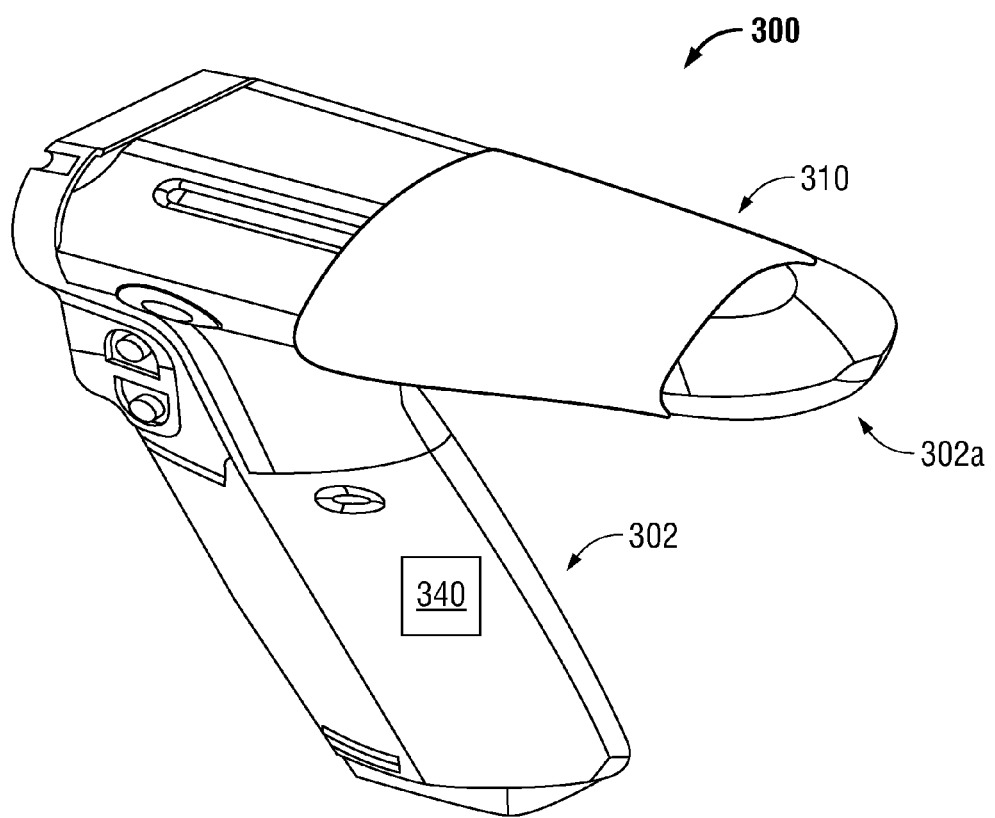
FIG. 3A is a perspective view of an electromechanical handheld surgical device in accordance with an embodiment of the present disclosure.
Figure 3B:
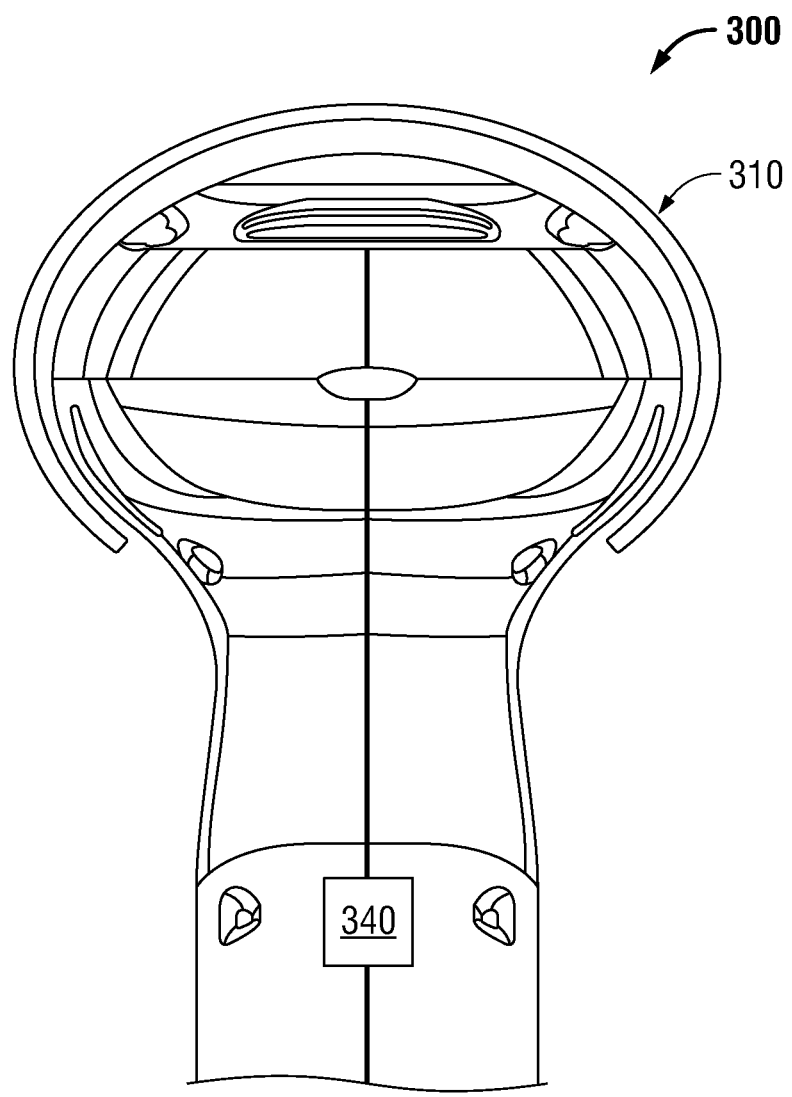
FIG. 3B is a rear view of the surgical device of FIG. 3A in accordance with an embodiment of the present disclosure.

FIGS. 3A and 3B illustrate an electromechanical handheld surgical device 300 in accordance with embodiments of the present disclosure. The electromechanical handheld surgical device 300 includes a handle 302, an upper handle portion 302a, a display screen 310, and an orientation detector 340. As shown in FIGS. 3A and 3B, handle 302 of electromechanical handheld surgical device 300 may have curved surfaces for ease of use, ergonomics, and/or esthetic purposes.

Handle 302 has an ergonomic shape suitable for a clinician to hold and enable use of electromechanical handheld surgical device 300. Handle 302 may also include a battery 450 to render electromechanical handheld surgical device 300 a portably powered electromechanical handheld surgical device. Handle 302 may further include at least one trigger to actuate an operation of an end effector (not shown) to perform a function thereof.

Upper handle portion 302a may be adapted to selectively connect and receive any end effectors, which have a specific connection portion configured for selective connection to upper handle portion 302a in order to perform surgical operations (e.g., desiccation, sealing, cautery, ablation, coagulation, etc.). In an embodiment, handle 302 may recognize what type of end effector is connected thereto. For this purpose, handle 302 may include a switch (which is not shown) or an electrical contact (which is not shown), which communicates with the end effector connected thereto. In an embodiment, when an end effector is connected to handle 302, a user of electromechanical handheld surgical device 300 may manually move a switch to a proper position to indicate which type of end effector is connected to handle 302. In another embodiment, electromechanical handheld surgical device 300 may communicate with the end effector connected to handle 302, via an electrical contact which transmits and/or receives analog or digital electrical signals to and from the end effector to recognize a type of the end effector.

Display screen 310 is fixedly attached around a proximal portion of electromechanical handheld surgical device 300. In an embodiment, display screen 310 may cover any portions of electromechanical handheld surgical device 300 except a lower handle portion and/or an end effector connecting portion of handle 302. The display screen 310 is flexible or curved so that display screen 310 can be affixed to the curved housing (e.g., upper handle portion 302a) of electromechanical handheld surgical device 300. In this way, the surface area or the coverage area of display screen 310 is greater than that of rigid display screens such as flat display screen 210 and flexible or curved display screen 310 may display more information than flat display screen 210.

Due to display screen 310 being flexible or curved, an overall size of electromechanical handheld surgical device 300 can be decreased, as compared to a device including flat display screen 210, because there is less wasted space within handle 302.

In an embodiment, display screen 310 may be an electronic paper based on electrophoretic or electrowetting technologies. In another embodiment, display screen 310 may be an organic light-emitting diode (OLED) flexible display screen or an active-matrix OLED (AMOLED) flexible display screen. This list of display screen 310 is not limited to the list above but may be any flexible display screen using any technologies available to the public.

Information of electromechanical handheld surgical device 300 may be displayed on display screen 310, when electromechanical handheld surgical device 300 is powered up and is not used or is not connected to any end effector. The information of electromechanical handheld surgical device 300 may include, for example, an end user license agreement ("EULA"), when electromechanical handheld surgical device 300 is registered to a surgical system or is used at the first time in its lifespan. The information of electromechanical handheld surgical device 300 may further include specification of electromechanical handheld surgical device 300, instructions how to use electromechanical handheld surgical device 300, labeling of electromechanical handheld surgical device 300, and any restrictions in using electromechanical handheld surgical device 300.

Display screen 310 may display a setting screen so that a user can set parameters of the electromechanical handheld surgical device. The parameters may include a regional setting, a language setting, a temporal setting, etc. When the regional setting is set, an appropriate time zone may be automatically selected based on the regional setting. When the language is set, display screen 310 may display information in the set language. In an embodiment, the setting screen may be displayed in two or more different languages including one default language, for example, English, and the set language so that, in the event a user accidently sets the language setting to a wrong language, the use is able to reset the language setting based on English or another predetermined default language.

In an embodiment, display screen 310 may be touch-sensitive so that display screen 310 may be used as an input device. When the setting screen is displayed on display screen 310, a user may select or set a parameter for each setting by clicking or touching an appropriate portion of display screen 310. In another embodiment, when electromechanical handheld surgical device 300 is to be registered, a user may have to press a button, which is displayed on display screen 310, to indicate that the user reads and agrees with the EULA.

In an embodiment, the displayed information on display screen 310 may be interface information of a type of an end effector, which is connected to handle 302. For example, when an ablation end effector is connected to handle 302, display screen 310 may display interface labels of the ablation end effector. The interface labels of the ablation end effector may include a proper frequency and a proper power level based on a type of tissue to be ablated. In this way, display screen 310 is able to display interface information of any end effector.

In another embodiment, the displayed information may be related to surgical operations. Information of surgical information may include status information, such as temporal status of surgical operation, characteristics information of a surgical site of a patient, and any notice or warning. The temporal status information may indicate a beginning, intermediate, and ending state, or a ready status. A user of electromechanical handheld surgical device 300 can perform proper operations based on the temporal status information. For example, when a staple end effector is connected to handle 302 and a correct amount or thickness of tissue is properly squeezed by a cartridge assembly and an anvil assembly of the staple end effector, display screen 310 displays status information indicating readiness of the tissue to be stapled so that the user of electromechanical handheld surgical device 300 triggers an actuator of handle 302 to perform a stapling process.

The characteristic information of a surgical site may include temperature, impedance, clarity, density, a type of tissue such as blood vessel, and any suitable information. In a case when a sealing end effector is connected to handle 302, a real part of impedance of tissue may be considered to control a level of power delivered to the tissue. Temperature of the tissue may also be considered in determining the real part of impedance of the tissue. Based on such displayed characteristic information, a clinician may determine a proper level of power, current, or voltage supplied to the sealing end effector. Also, based on the displayed real part of the impedance, a user of the electromechanical handheld surgical device can determine a mode of the sealing process among constant current, constant power, and constant voltage modes for the sealing process.

When electromechanical handheld surgical device 300 transmits electrosurgical energy to an end effector, which is beyond what is intended or necessary for the surgical operation, display screen 310 may display a warning message indicating that electrosurgical energy is being overly transmitted or close to a maximum level for the surgical operation. In this case, addition to the displayed warning message, electromechanical handheld surgical device 300 may simultaneously generate an audio sound alerting a clinician so that the clinician can immediately adjust the level of electrosurgical energy to a proper level or shut off the power. The warning message may be displayed with high contrast so that the user of electromechanical handheld surgical device 300 cannot miss the warning message.

In embodiments, display screen 310 may also display instructions for a surgical operation. When a series of sub-operations are needed to perform the surgical operation, display screen 310 displays instructions based on a temporal stage of the surgical operation so that a clinician using electromechanical handheld surgical device 300 does not have to remember specifics about using electromechanical handheld surgical device 300 for the surgical operation but follows displayed instructions. For example, when more power is needed to advance the surgical operation, display screen 310 displays to the clinician instructions to increase the level of power to a predetermined level or by a predetermined amount. The displayed information may remain until the instructions are fully performed.

Figure 4:
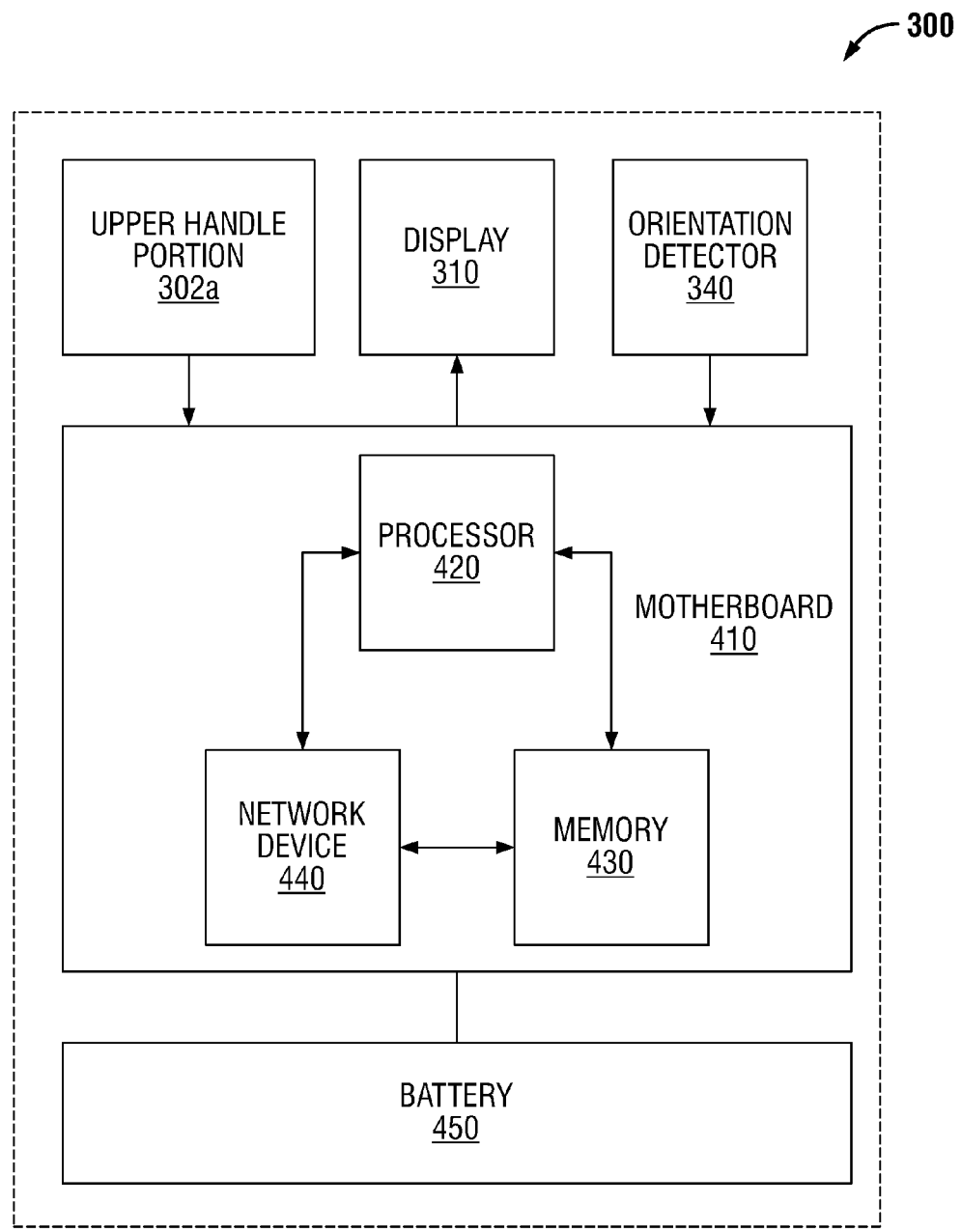
FIG. 4 is a block diagram for the surgical device of FIG. 3A in accordance with embodiments of the present disclosure.

With reference to FIGS. 3A, 3B, and 4, orientation detector 340 of electromechanical handheld surgical device 300 detects an orientation of electromechanical handheld surgical device 300 with respect to a reference orientation. The direction of the gravitational force or the opposite direction to the gravitational force may be the reference orientation. In other words, upright standing position of electromechanical handheld surgical device 300 may be the reference orientation. The orientation detector 340 may be a 3-axis accelerometer, gyroscope, 3-axis magnetometer, or any other device that detects an orientation. The orientation detector 340 may be placed in handle 302 or anywhere inside of electromechanical handheld surgical device 300.

FIG. 3B illustrates a rear view of electromechanical handheld surgical device 300 of FIG. 3A. Display screen 310 smoothly covers the ergonomic design of electromechanical handheld surgical device 300. Display screen 310 may also cover the non-handle part (e.g., upper handle portion 302a) of electromechanical handheld surgical device 300. As compared with flat display screen 210 of FIG. 2, the surface area or display area of flexible or curved display screen 310 is enhanced or enlarged from that of flat display screen 210. As a result, electromechanical handheld surgical device 300 may be reduced in size compared with electromechanical handheld surgical device 200.

In embodiments, display screen 310 may cover upper handle portion 302a entirely or partially. For example, display screen 310 may cover the surface of upper handle portion 302a by at least 30° degrees or in other words, at least 15° in the left and right from the top of upper handle portion 302a. Display screen 310 may also cover upper handle portion 302a by at least 45°, 60°, 90°, 180°, 270°, or 360°. In an aspect, display screen 310 may partially or wholly cover the surface of upper handle portion 302a, asymmetrically about the top of upper handle portion 302a.

FIG. 4 illustrates a block diagram of electromechanical handheld surgical device 300 of FIGS. 3A and 3B in accordance with embodiments of the present disclosure. The electromechanical handheld surgical device 300 may further include a motherboard 410, display screen 310, and orientation detector 340. The motherboard 410 has a processor 420, a memory 430, and a network device 440. The listed components are all connected to communicate with each other via a system bus of the motherboard. The processor 420, memory 430, and network device 440 may be inserted to a socket of motherboard 410 or integrated into motherboard 410. The motherboard 410 may be a printed circuit board.

The processor 420 is used for performing commands from programs or software. The processor 420 may be a central processing unit (CPU), a graphical processing unit (GPU), digital signal processor (DSP), or microprocessor. All or part of processor 420 may be implemented by a field programmable gate array (FPGA), an application specific integrated circuit (ASIC), a digital signal processor (DSP), a microcontroller, and/or any other suitable logic circuit.

The memory 430 is used for storing data and programs. The memory 430 may include a read-only memory (ROM), random access memory (RAM), flash memory, universal serial bus (USB) memory, or any combination thereof. ROM is used to store instructions (e.g., batch processes) for processor 420 to execute batch processes when electromechanical handheld surgical device 300 is booted up or powered on. RAM is used to store data and processor-executable commands to run programs.

The network device 440 is used for communicating with a device remote from electromechanical handheld surgical device 300. When network device 440 is connected to a network, network device 440 may be used to download update programs to update new functionalities of electromechanical handheld surgical device 300 or transmit information of electromechanical handheld surgical device 300 to a remote device. After the update, processor 420 causes display screen 310 to display the updated functionalities on the screen.

The processor 420 performs functions described above with respect to handle 302, display screen 310, and orientation detector 340. When an end effector is connected to handle 302, information about the connected end effector, such as a type, is transmitted to processor 420. The processor 420 then causes display screen 310 to display corresponding information about the end effector.

When a change of orientation of electromechanical handheld surgical device 300 is detected by orientation detector 340, processor 420 receives information of the changed orientation. Then processor 420 determines which portion of display screen 310 is a proper place to display information for optimal visualization by the end user. In particular, processor 420 determines a starting location for displaying information and a displaying direction to display information. In an embodiment, processor 420 may use user's preferences to determine the displaying direction and the starting location.

Figure 5A:
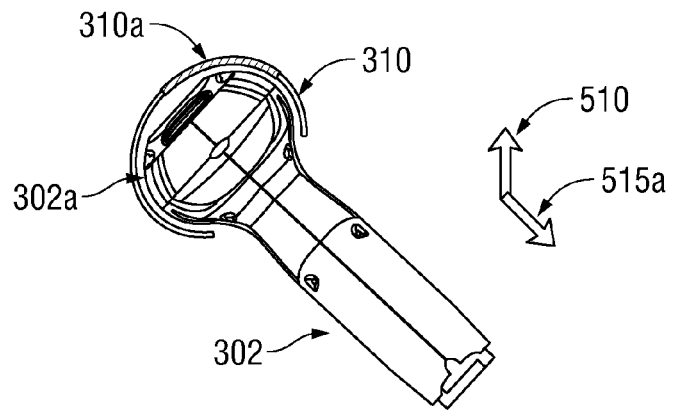
FIGS. 5A-5C are rear views illustrating various orientations of the electromechanical handheld surgical device in accordance with an embodiment of the present disclosure.
Figure 5B:
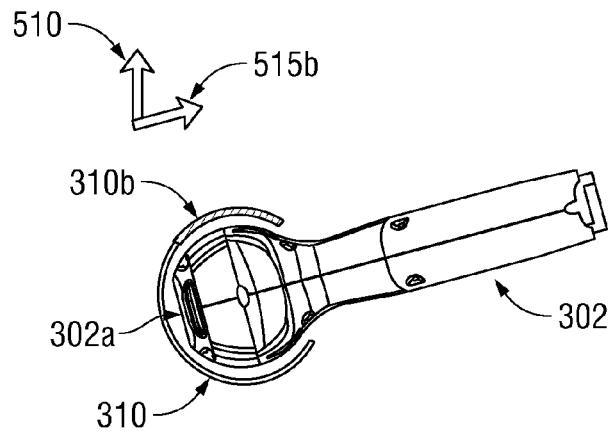
Figure 5C:
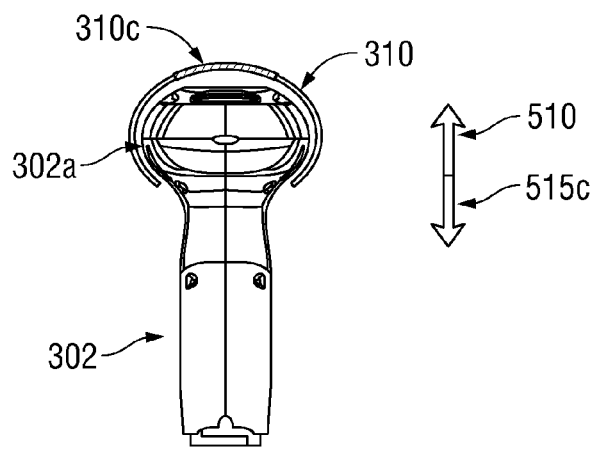

FIGS. 5A-5C illustrate how to determine the starting location for displaying information with respect to the reference orientation in accordance with embodiments of the present disclosure. As shown in FIG. 5A, upper handle portion 302a of electromechanical handheld surgical device 300 is inclined toward the left. In this situation, orientation detector 340 reports a handle orientation 515a of electromechanical handheld surgical device 300, i.e., the left inclination, to processor 420, which determines an angle between reference orientation 510 and handle orientation 515 of electromechanical handheld surgical device 300. Based on this angle, processor 420 determines a portion of display screen 310 for display to the end user, namely, portion 310a of display screen 310.

The display portion 310a of display screen 310 has two end sections or boundaries. Information may be displayed from right end section to the left end section or vice versa. A user of electromechanical handheld surgical device 300 may have to choose a direction for displaying. In an embodiment, when the user is left-handed, the user may want to display information from the left end section to the right end section, or when the user is right-handed, the user may want to display information from the right end section to the left end section. In this way, processor 420 may determine display portion 310a of display screen 310 for displaying information and the starting location based on a user's preference or setting.

FIG. 5B illustrates that upper handle portion 302a of electromechanical handheld surgical device 300 is lower than the handle portion and declined toward the left. As shown, electromechanical handheld surgical device 300 defines a handle orientation 515b relative to reference orientation 510, and processor 420 determines a display portion 310b of display screen 310 for displaying information. Further, processor 420 determines which direction is used for displaying information as described above with respect to FIG. 5A.

FIG. 5C also illustrates that upper handle portion 302a of electromechanical handheld surgical device 300 is in line with reference orientation 510, meaning that reference orientation 510 is opposite to a handle orientation 515c of electromechanical handheld surgical device 300. In this situation, information is displayed on top portion of display screen 310. As described in FIGS. 5A and 5B, the displaying direction is also determined by processor 420 based on a user's preference or a displaying direction setting.

In an embodiment, a user may set a preferred angle so that information is displayed starting from a location of display screen 310 at an angle, which is substantially equivalent to a preferred angle or to reference orientation 510. The preferred angle may be based on a height of a user's eye with respect to the location where the user handles electromechanical handheld surgical device 300 or based on a user's preference.

In another embodiment, a user may set a range of display screen 310 on which information is displayed. That will determine the area of display screen 310 displaying information thereon. This is referenced by 310a, 310b, and 310c in FIGS. 5A-5C, respectively.

Figure 6:
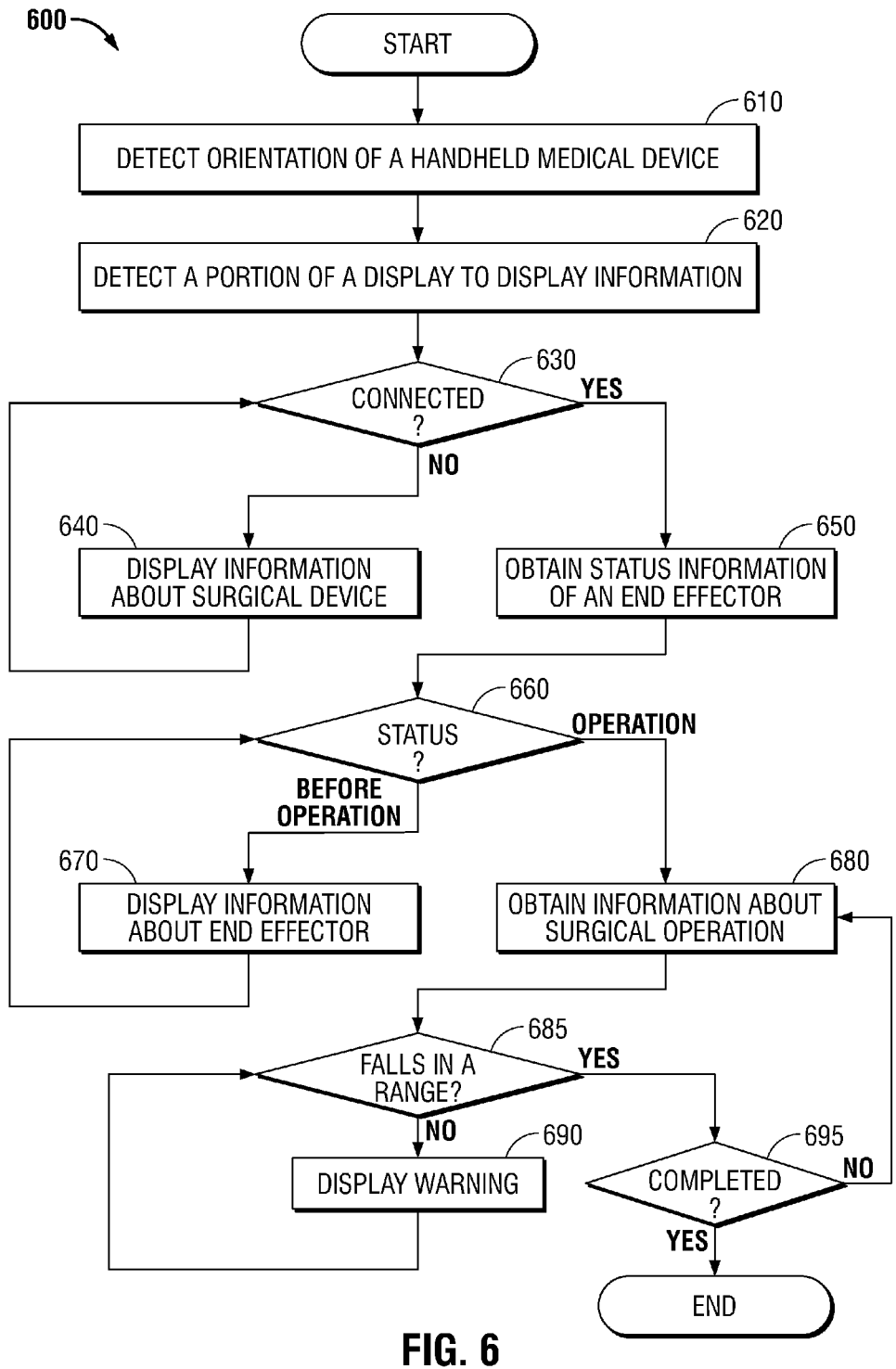
FIG. 6 is a flow chart for displaying information on a display screen of the electromechanical handheld surgical device in accordance with an embodiment of the present disclosure.

FIG. 6 is a flowchart of a method 600 for displaying information on a display screen of an electromechanical handheld surgical device in accordance with the present disclosure. In particular, method 600 for displaying information on the display screen may use only a portion of the total area of the display screen. The method 600 includes, at step 610, detecting an orientation of an electromechanical handheld surgical device by an orientation detector, such as by a 3-axis accelerometer, gyroscope, 3-axis magnetometer, or any other device that detects an orientation, and transmitting the detected orientation to processor 420 of electromechanical handheld surgical device 300.

In step 620, processor 420 determines a displaying portion of the display screen 310 based on the detected orientation of electromechanical handheld surgical device 300. In an embodiment, processor 420 also determines a displaying direction based on a setting by a user.

In step 630, it is determined whether an end effector is connected to a connecting portion of electromechanical handheld surgical device 300. When it is determined that the end effector is not connected, the display screen displays such information of electromechanical handheld surgical device 300 on the determined portion of display screen in step 640. The information of electromechanical handheld surgical device 300 may be EULA, specification, version of software that is installed in electromechanical handheld surgical device 300, a log of software update, or any relevant information of electromechanical handheld surgical device 300. Then method 600 keeps checking whether an end effector is connected in step 630. In an aspect, the information may be displayed for a predetermined time and disappear. In another aspect, the information may be scrolled to continuously display the entire content of the information.

When it is determined that end effector is connected in step 630, processor 420 receives information of end effector in step 650. In particular, processor 420 may obtain a type of the end effector from the end effector, which connected to the electromechanical handheld surgical device 300, and retrieve detail information about the type of the end effector from a memory thereof. The detail information of possible end effectors may be obtained through software updates via a network device.

After step 650, method 600 proceeds to check a status of surgical operation in step 660. When it is determined that the status indicates that the operation has not started yet, the display screen then displays information of the end effector on the determined display portion of display screen in step 670. The displayed information in step 670 may be displayed for a predetermined time and display screen 310 may display the information periodically. The method 600 keeps checking status in step 660 until the operation starts.

When it is determined that the status indicates that operation has started in step 660, the display screen 310 then displays information of the surgical operation on the determined portion of display screen 310. The information of the surgical operation may include instructions to the clinician based on the surgical operation, information of a surgical site, etc. The instructions may include instructions based on a temporal stage of the surgical operation so that a clinician using electromechanical handheld surgical device 300 does not have to remember specifics about the surgical operation. For example, when more power or a different frequency of the electrosurgical energy is needed to advance the surgical operation, display screen 310 displays such instructions. The displayed information may remain until the instructions are fully performed. The information of the surgical site (e.g., tissue to be treated) may include temperature, impedance, clarity, or a type of the surgical site and voltage, current, power, or ultrasonic frequency applied to the surgical site.

In step 685, processor 420 determines whether a parameter related to the surgical operation falls within an acceptable range. The parameter may be a real part of impedance of tissue, amplitude of power, current or voltage, or any other surgically relevant parameter. When a power is lower than the minimum level, intended surgical effects cannot be obtained, or when the power is greater than the maximum level, unintended damages may be done to the surgical site (e.g., tissue or internal organs). The parameter may be a completion of a staple firing sequence, that a stapler end effector has hit an end stop or an obstruction.

When it is determined, by processor 420, that the parameter does not fall within an acceptable range in step 685, display screen 310 may display a warning thereon with high contrast in step 690. In an embodiment, when the parameter exceeds the maximum, display screen 310 may display the warning with further emphasis graphically or electromechanical handheld surgical device 300 may generate an audible warning. Then processor 420 keeps checking range of the parameter in step 685 and displaying warning in step 690.

In an embodiment, in step 685, processor 420 checks all parameters with their corresponding acceptable ranges. If any one of the parameters does not fall within its acceptable range, display screen 310 displays a warning including the parameter name, the value of the parameter, and acceptable range in step 690. In this way, a user of electromechanical handheld surgical device 300 can see which parameter is not met and provide a suggestion as to what action is needed to remedy the situation. The warning may further include instructions so that the clinician of electromechanical handheld surgical device 300 has to follow to make the parameter fall within the acceptable range.

When processor 420 determines that the parameter does fall within acceptable range in step 685, method advances to step 695, in which processor 420 determines whether the surgical operation is complete. When processor 420 determines that the surgical operation is not complete, display screen 310 keeps displaying information of the surgical operation until the surgical operation is complete. When processor 420 determines that the surgical operation is complete, method 600 is ended and display screen 310 displays a corresponding message on its screen.

Figure 7:
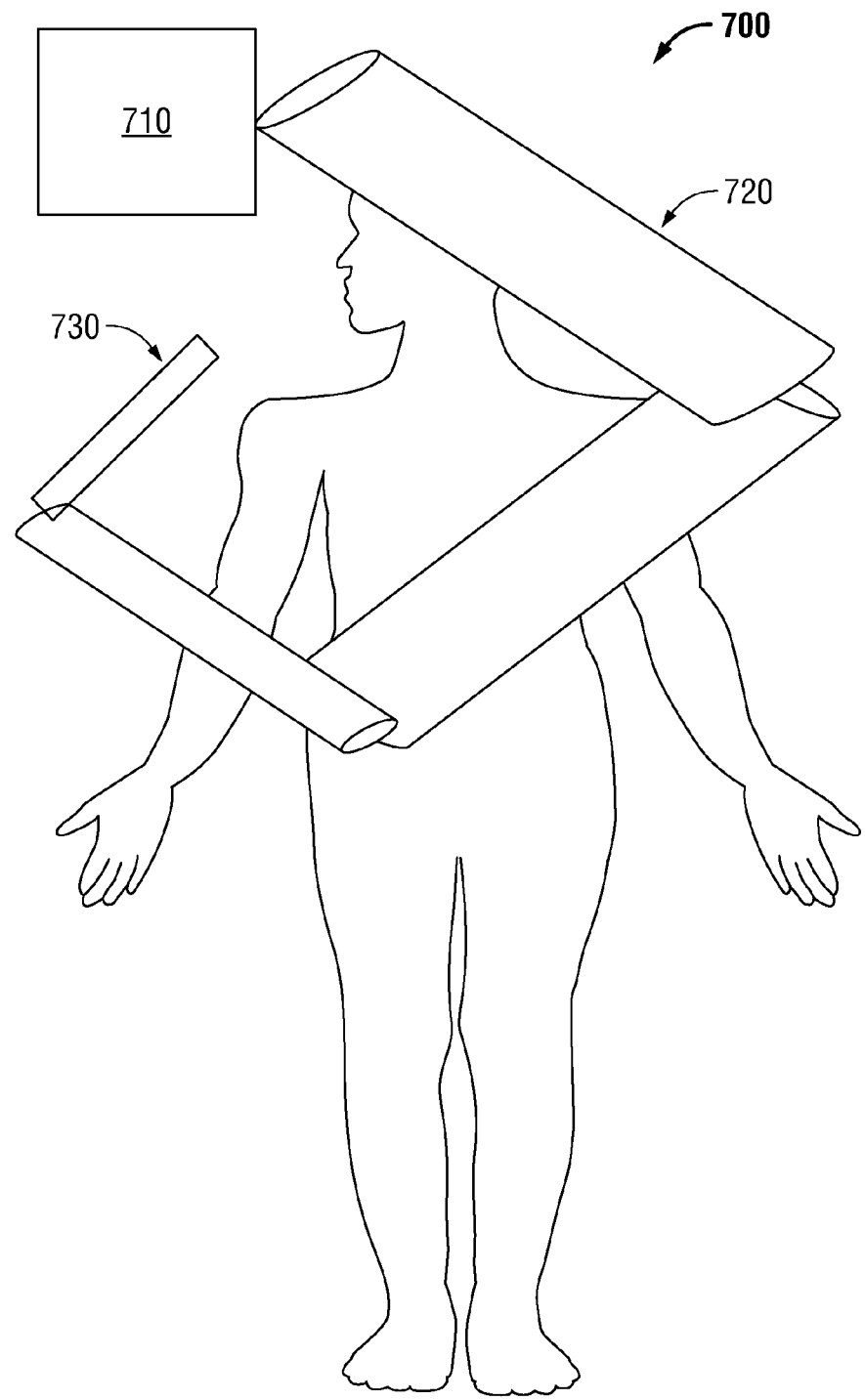
FIG. 7 is a surgical system of the prior art.

FIG. 7 illustrates a surgical system 700 of the prior art. The surgical system 700 has a support 710 that does not move or is fixed with respect to ground. The surgical system 700 further includes a robot arm 720 and an electromechanical surgical device 730. The robot arm 720 is operatively connected with electromechanical surgical device 730. The robot arm 720 has one or more joints such that electromechanical surgical device 730 may be freely movable to a surgical site of a patient under robot arm 720.

As shown in the FIG. 7, when electromechanical surgical device 730 is placed over the surgical site of the patient, robot arm 720 is inevitably covering some portions of the patient. That portion of robot arm 720 and/or electromechanical surgical device 730 may obstruct a view of a clinician who is operating surgical system 700. In a certain situation, obstruction against a clinician's view causes the clinician to move the clinician's head or body so that the clinician has a clear view to the surgical site. However, such clinician's movements may cause an unwanted movement of robot arm 720 or electromechanical surgical device 730.

Figure 8A:
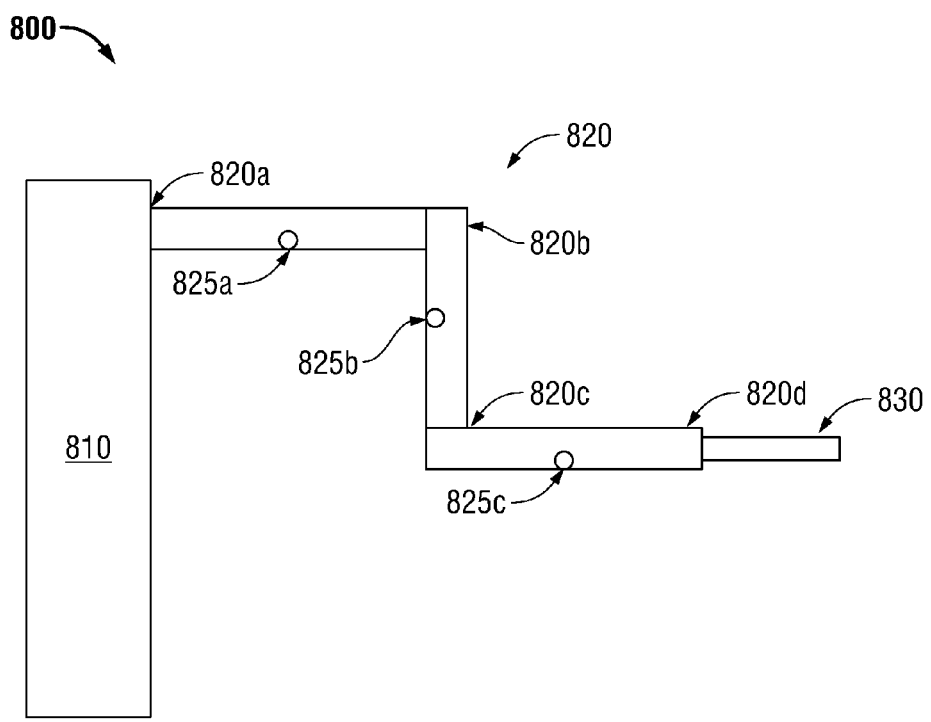
FIG. 8A is a block diagram of a surgical system including flexible or curved display screens in accordance with embodiments of the present disclosure.

FIG. 8A shows a surgical system 800 in accordance with embodiments of the present disclosure. The surgical system 800 is designed to remove obstruction of a clinician's view.

The surgical system 800 includes a support 810, a robot arm 820, and an electromechanical handheld surgical device 830.

The support 810 is configured not to move or is fixed with respect to ground, a wall, or a bed to which support 810 is affixed such that any movement of robot arm 820 does not cause a movement of support 810. Robot arm 820 is operatively connected to support 810.

Outside joints 820*a* and 820*d* of robot arm 820 are configured to operatively connect robot arm 820 with support 810 and electromechanical handheld surgical device 830, respectively. Inside joints 820*b* and 820*c* are configured to operatively connect each arm of robot arm 820. The inside and outside joints 820*a*-820*d* are configured in a way such that electromechanical handheld surgical device 830 may be freely movable horizontally and vertically toward any surgical site of a patient under robot arm 820. The number of inside joints 820*b* and 820*c* of robot arm 820 is not limited to two as shown in FIG. 8A but can be less than or greater than two.

Each portion of robot arm 820 may include a sensor 825*a*, 825*b*, or 825*c*. The sensors 825*a*-825*c* are configured to sense a view under the corresponding arms. In an embodiment, sensors 825*a*-825*c* are visible light sensors, which sense visible light reflected from portions of the patient under the corresponding arm. In another embodiment, sensors 825*a*-825*c* are any sensor that can be used to sense images of the patient under the arms.

The surgical system 800 also includes a processor and a memory, which are not shown in FIG. 8A. The processor and the memory perform any processes suitable for surgical system 800, similar to the processor 420 and the memory 430 described above in FIG. 4.

The surgical system 800 further includes a plurality of flexible or curved display screens (which are not shown in FIG. 8A), each flexible or curved display screen is fixedly attached to a corresponding portion of robot arm 820. The flexible or curved display screen may cover a small portion of robot arm 820 or the whole surface of robot arm 820.

Each of sensors 825*a*-825*c* senses a view or takes images under the corresponding portion of robot arm 820 and transmits to the processor and the memory of surgical system 800. The processor performs image processing on the sensed view or images and controls the plurality of flexible or curved display screens to display screen the processed views on each display screen of the plurality of flexible or curved display screens.

Figure 8B:
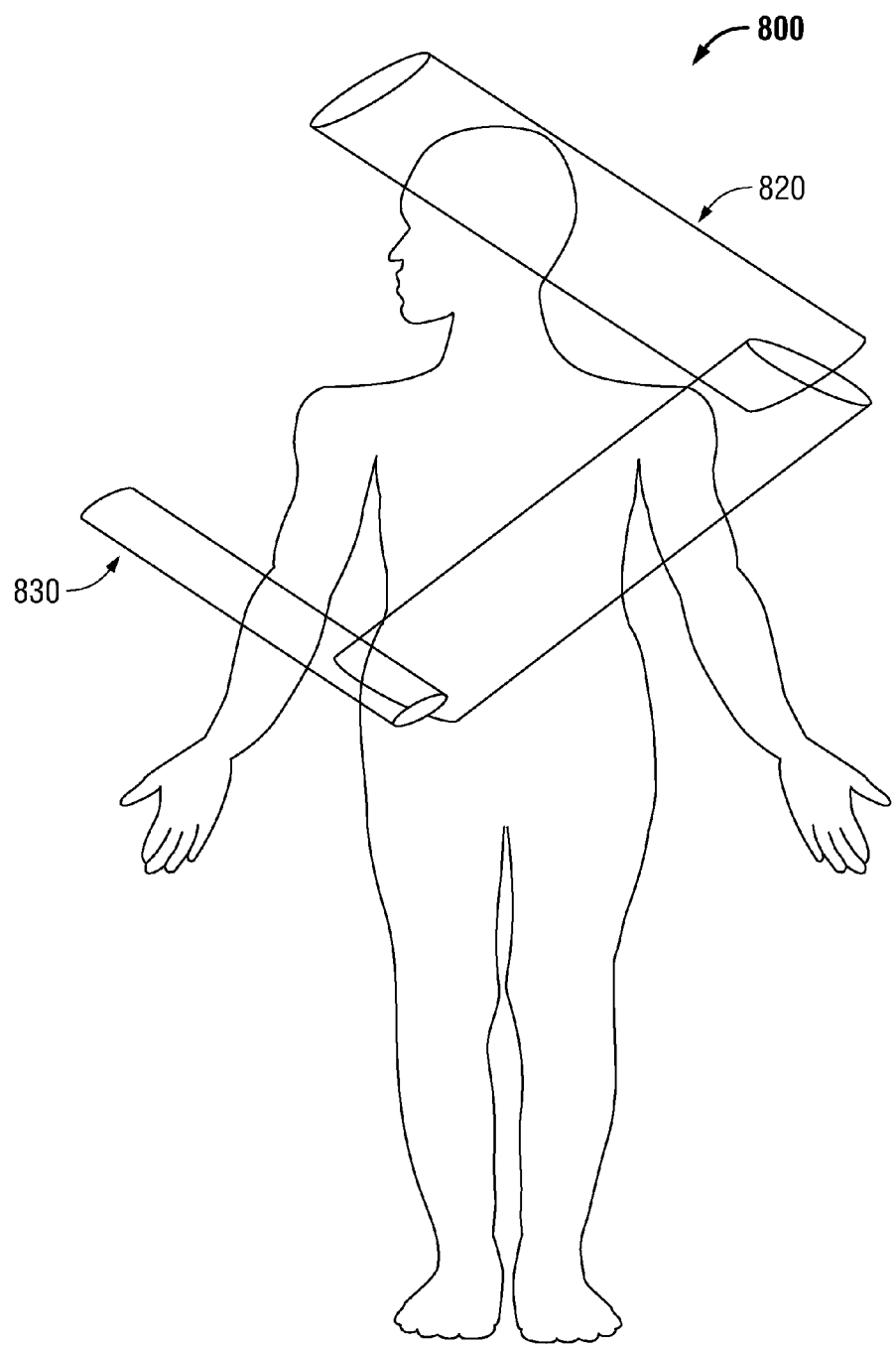
FIG. 8B is a schematic illustration of the surgical system of FIG. 8A over a patient.

As described with respect to FIGS. 5A-5C, the processor may determine a display starting location for displaying and a portion of each flexible or curved display screen for displaying the processed view. As a result, robot arm 820 may appear to be substantially transparent to the clinician who operates surgical system 800 as shown in FIG. 8B.

In an embodiment, the processor may include a plurality of processors, each of which individually receives sensed views from the corresponding sensor, processes to generate images visible to the clinician who operates surgical system 800, and causes the flexible or curved display screen to display the visible images on corresponding screen of the plurality of flexible or curved display screens.

With respect to determining the starting location and information displayed on the flexible or curved display screens, method 600 of FIG. 6 may be utilized in surgical system 800 of FIG. 8A.

It will be understood that various modifications may be made to the embodiments of the presently disclosed adapter assemblies. Therefore, the above description should not be construed as limiting, but merely as exemplifications of embodiments. Those skilled in the art will envision other modifications within the scope and spirit of the present disclosure.

What is claimed is:

1. An electromechanical handheld surgical device, comprising:
a housing enclosing and including:
a processor;
a memory coupled to the processor and storing instructions; and
an orientation detector configured to detect orientation of the electromechanical handheld surgical device with respect to a reference direction; and
a non-planar display screen fixedly attached around a portion of the housing and configured to display information, wherein the display screen has more than one display portion, wherein the non-planar display screen covers an upper surface of the housing by at least 15 degrees to the left side and to the right side of the housing, from a top of the upper surface of the housing,
wherein the instructions, when executed by the processor, cause the non-planar display screen to display the information on a portion of the non-planar display screen,
wherein the instructions, when executed by the processor, move the information from a first display portion of the non-planar display screen to a second display portion, which is determined only based on a change in the detected orientation, and
wherein a starting location for displaying the information is determined based on a display direction setting entered by a user of the electromechanical handheld surgical device, wherein the starting location is at least one of a right side of the housing or a left side of the housing.

2. The electromechanical handheld surgical device according to claim 1, wherein the display portion of the non-planar display screen is determined with respect to the reference direction.

3. The electromechanical handheld surgical device according to claim 1, wherein the reference direction is in line with a direction of gravity.

4. The electromechanical handheld surgical device according to claim 1, wherein a starting location of the display portion of the non-planar display screen is located on the non-planar display screen at a constant angle with respect to the reference direction.

5. The electromechanical handheld surgical device according to claim 1, wherein a middle of the display portion of the non-planar display screen is located on the non-planar display screen at a constant angle with respect to the reference direction.

6. The electromechanical handheld surgical device according to claim 1, wherein an ending location of the display portion of the non-planar display screen is located on the non-planar display screen at a constant angle with respect to the reference direction.

7. The electromechanical handheld surgical device according to claim 1, wherein the information is related to a surgical operation when the electromechanical handheld surgical device is used in the surgical operation.

8. The electromechanical handheld surgical device according to claim 1, wherein the information changes based on a status of a surgical operation.

9. The electromechanical handheld surgical device according to claim 1, wherein the information is related to the electromechanical handheld surgical device before the electromechanical handheld surgical device is used in a surgical operation.

10. The electromechanical handheld surgical device according to claim 1, wherein the information is related to a portion of tissue to which a surgical operation is performed.

11. The electromechanical handheld surgical device according to claim 1, wherein the non-planar display screen is touch-sensitive.

12. The electromechanical handheld surgical device according to claim 11, wherein the displayed information is scrolled based on a direction of a touch to the non-planar display screen.

13. The electromechanical handheld surgical device according to claim 1, wherein the non-planar display screen is curved.

14. The electromechanical handheld surgical device according to claim 1, wherein the non-planar display screen is flexible.

15. The electromechanical handheld surgical device according to claim 1, wherein the non-planar display screen extends greater than about 15° along a portion of the housing.

16. The electromechanical handheld surgical device according to claim 1, wherein a range for displaying the information is set based on a range setting.

17. A method for displaying information on a non-planar display screen fixedly attached around a portion of an electromechanical handheld surgical device, wherein the display screen has more than one display portion, the method comprising:
obtaining an orientation with respect to a reference orientation from an orientation detector of the electromechanical handheld surgical device;
determining a portion of the non-planar display screen based on the orientation and with respect to the reference orientation;
retrieving status information from the electromechanical handheld surgical device;
displaying information on the portion of the non-planar display screen based on the status information of the electromechanical handheld surgical device;
moving the portion of the non-planar display screen displaying the information from a first display portion of the non-planar display screen to a second display portion, which is determined only based on a change in the detected orientation, and
determining a starting location for displaying the information is determined based on a display direction setting entered by a user of the electromechanical handheld surgical device, wherein the starting location is at least one of a right side of the housing or a left side of the housing, wherein the non-planar display screen covers an upper surface of the housing by at least 15 degrees to the left side and to the right side of the housing, from a top of the upper surface of the housing.

18. The method according to claim 17, wherein displaying information includes displaying information about the electromechanical handheld surgical device when the status information indicates that the electromechanical handheld surgical device is not used in a surgical operation.

19. The method according to claim 17, wherein displaying information includes displaying information about a surgical operation when the status information indicates that the electromechanical handheld surgical device is being used in the surgical operation.

20. The method according to claim 17, wherein displaying information includes displaying information related to a portion of tissue to which a surgical operation is performed, when the status information indicates that the electromechanical handheld surgical device is used in the surgical operation.

21. The method according to claim 17, wherein the reference orientation is in line with a direction of gravity.

22. The method according to claim 17, further comprising determining whether an end effector is connected to the electromechanical handheld surgical device.

23. An electromechanical surgical system comprising:
a support immovably fixed to a surface;
an electromechanical surgical device configured to perform a surgical operation;
a plurality of arms serially connected to each other, one end of the plurality of arms being connected to the electromechanical surgical device and the other end of the plurality of arms being connected to the support; and
a plurality of non-planar display screens, each one of the plurality of non-planar display screens being fixedly attached around a corresponding one of the plurality of arms,
wherein each of the plurality of arms includes a sensor configured to periodically capture an image of a view under each arm, and an orientation detector configured to detect an orientation of each arm with respect to a reference orientation, and
wherein the non-planar display screen corresponding to each arm displays a captured image on a portion of the display screen of each arm based on the detected orientation.

* * * * *